United States Patent
Majercak et al.

(10) Patent No.: US 10,357,275 B2
(45) Date of Patent: Jul. 23, 2019

(54) DUAL-BASKET SELF-CENTERING ROTATIONAL DEVICE FOR TREATMENT OF ARTERIAL OCCLUSIVE DISEASE WITH INFINITELY ADJUSTABLE CUTTING SIZE

(71) Applicant: CORDIS CORPORATION, Fremont, CA (US)

(72) Inventors: David Majercak, Livermoore, CA (US); Wendy Ann Young, Cupertino, CA (US)

(73) Assignee: CARDINAL HEALTH SWITZERLAND 515 GMBH, Bar Zug (CH)

( * ) Notice: Subject to any disclaimer, the term of this patent is extended or adjusted under 35 U.S.C. 154(b) by 208 days.

(21) Appl. No.: 14/752,630

(22) Filed: Jun. 26, 2015

(65) Prior Publication Data

US 2016/0374714 A1     Dec. 29, 2016

(51) Int. Cl.
*A61B 17/3207* (2006.01)
*A61B 17/22* (2006.01)
*A61B 17/00* (2006.01)

(52) U.S. Cl.
CPC .......... *A61B 17/320725* (2013.01); *A61B 17/320758* (2013.01); *A61B 2017/00867* (2013.01); *A61B 2017/00986* (2013.01); *A61B 2017/22079* (2013.01); *A61B 2217/007* (2013.01)

(58) Field of Classification Search
CPC .... A61B 17/320725; A61B 17/320758; A61B 2017/00867; A61B 2017/22079; A61B 2217/007
See application file for complete search history.

(56) References Cited

U.S. PATENT DOCUMENTS

| | | | | |
|---|---|---|---|---|
| 5,030,201 A | * | 7/1991 | Palestrant | A61B 17/320725 600/568 |
| 5,059,193 A | * | 10/1991 | Kuslich | F16B 13/061 606/247 |
| 5,716,325 A | * | 2/1998 | Bonutti | A61B 17/0218 600/153 |
| 6,030,406 A | * | 2/2000 | Davis | A61B 17/00008 604/104 |
| 6,280,456 B1 | * | 8/2001 | Scribner | A61B 10/025 606/192 |
| 6,565,588 B1 | | 5/2003 | Clement et al. | |
| 6,676,665 B2 | * | 1/2004 | Foley | A61B 17/025 600/201 |
| 7,270,673 B2 | * | 9/2007 | Yee | A61B 17/320725 606/159 |
| 7,674,272 B2 | | 3/2010 | Torrance et al. | |
| 8,377,037 B2 | | 2/2013 | Sachdeva et al. | |

(Continued)

OTHER PUBLICATIONS

Mood G.R., et al., "Atherectomy in the Treatment of Lower-Extremity Peripheral Artery Disease: A Critical Review," Vascular Disease Management, Oct. 2013, vol. 10 (10), pp. E192-E197.

*Primary Examiner* — Julie A Szpira
(74) *Attorney, Agent, or Firm* — Nada J. Ardeleanu

(57) ABSTRACT

An system for treating arterial occlusive disease with rotating cutting baskets whose outer diameter can be infinitely adjusted to adjust by the operator for precise excision of plaque buildup in the body vessel.

20 Claims, 6 Drawing Sheets
(1 of 6 Drawing Sheet(s) Filed in Color)

(56) References Cited

U.S. PATENT DOCUMENTS

| | | | | |
|---|---|---|---|---|
| 2002/0010487 A1* | 1/2002 | Evans | ............... | A61B 17/221 606/180 |
| 2003/0009130 A1* | 1/2003 | Stecker | ............... | A61M 1/0084 604/104 |
| 2005/0027245 A1* | 2/2005 | Sachdeva | ........... | A61B 1/00082 604/95.05 |
| 2006/0184192 A1* | 8/2006 | Markworth | ........ | A61B 17/1659 606/198 |
| 2006/0264896 A1* | 11/2006 | Palmer | ................ | A61B 10/025 604/506 |

\* cited by examiner

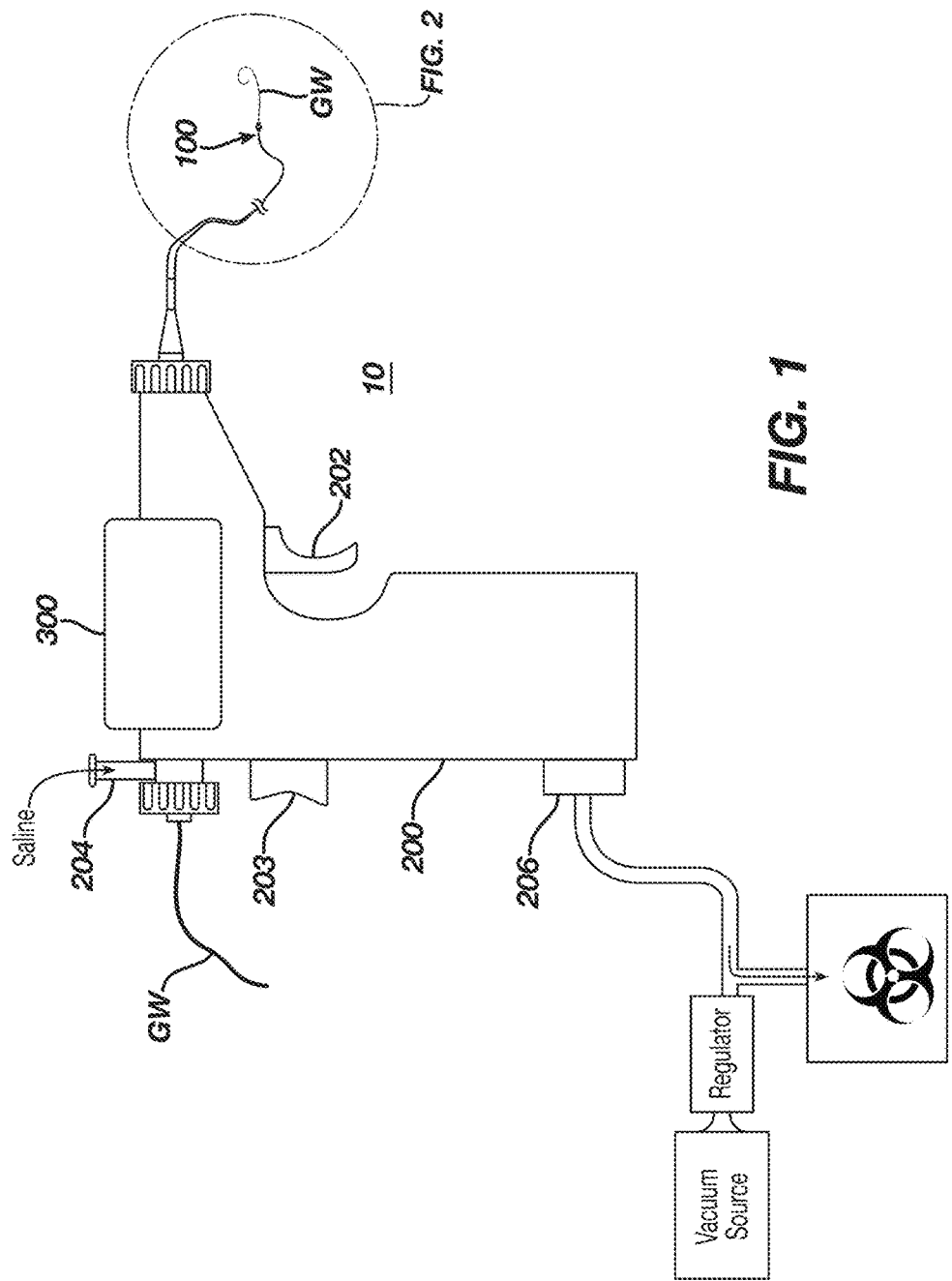

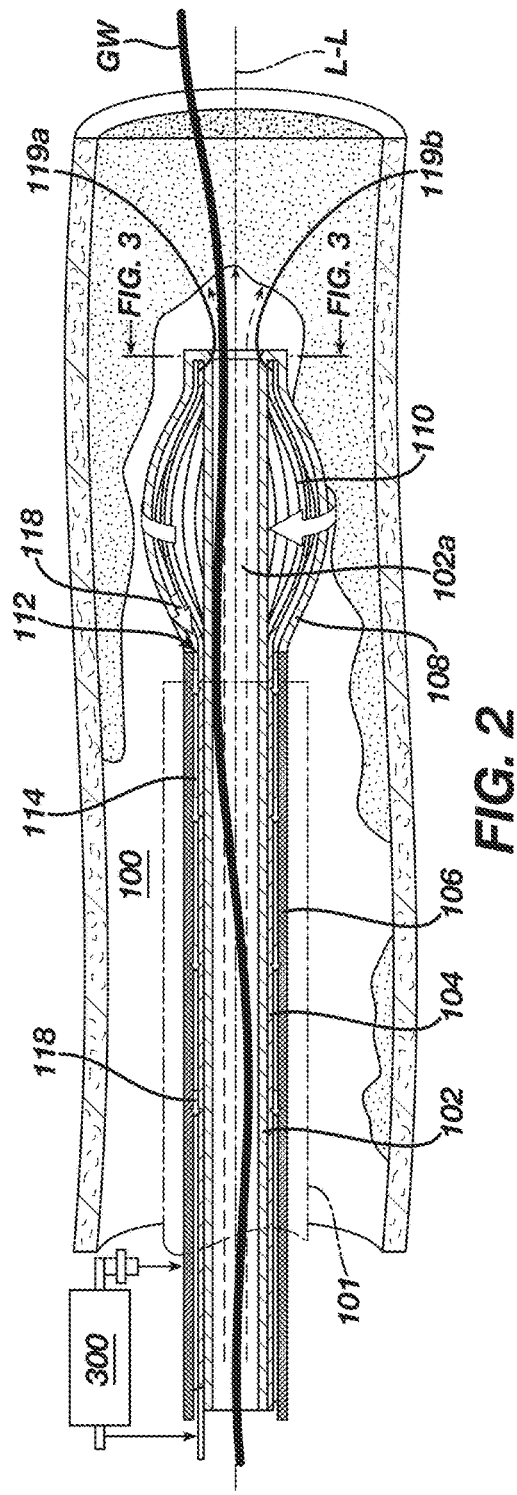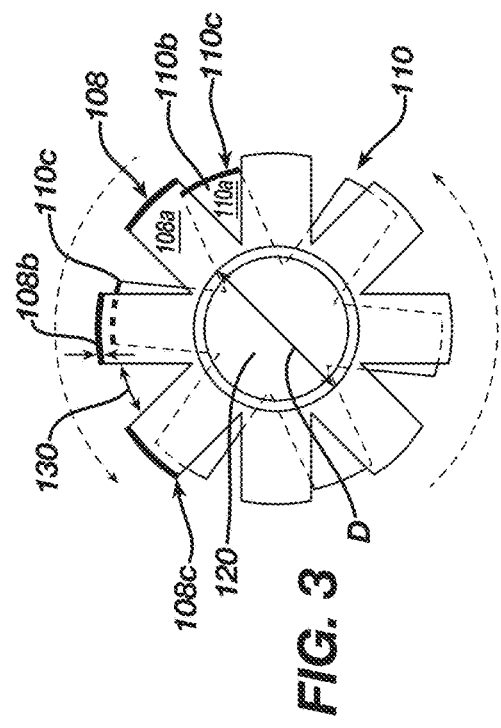

DUAL-BASKET SELF-CENTERING ROTATIONAL DEVICE FOR TREATMENT OF ARTERIAL OCCLUSIVE DISEASE WITH INFINITELY ADJUSTABLE CUTTING SIZE

BACKGROUND

For certain arterial diseases (e.g., peripheral arteries including the iliac, femoral, popliteal and tibial arteries) where plaques have built up onto the internal surface of blood vessel walls or thrombus in some cases (i.e., arterial occlusive disease), it is known to use a variety of techniques to improve blood flow through these vessels including, for example, angioplasty, stents or atherectomy. Angioplasty or stenting is believed to be ineffective when plaques may include irregular, loose or calcified deposits as these techniques simply compress the plaques further into the blood vessel walls with the attendant risk of vascular injuries. Atherectomy, on the other hand, where the plaque is physically removed, is believed to be more effective for calcified, fibrotic, as well as soft or longer lesions or lesions involving side branches in the peripheral arteries. The benefit of atherectomy is believed to arise from a reduction of plaque burden on the arterial wall that apparently does not affect the rest of the vessel walls post treatment.

Currently, several atherectomy devices are available on the market with FDA approval. These devices are categorized as laser ablation, orbital, rotational or directional atherectomy devices. Examples of such devices are described in U.S. Pat. Nos. 6,565,588; 7,674,272; 8,377,037; and "Atherectomy in the Treatment of Lower-Extremity Peripheral Artery Disease: A Critical Review" by Girish R. Mood, Md., Juyong Lee, Md., PhD, Lawrence A. Garcia, Md.; St. Elizabeth's Medical Center, Tufts University School of Medicine, Division of Interventional Cardiology and Vascular Medicine, Boston, Mass. (2013).

It is believed that some of these devices may facilitate the risk of plaque dissection due to the non-symmetrical cutting mechanism geometries and operational parameters. Some of these devices may not be as precisely controlled during the procedure due to the high rotational speed of the cutting tip or the non-symmetrical orientation of the cutting tip to the arterial vessel, which may lead to a phenomenon known as "whipping" of the atherectomy catheter. Whipping of the catheter may cause serious injuries including puncture of the artery.

SUMMARY OF THE DISCLOSURE

Recognizing these shortcomings of the aforementioned prior art, we have devised a heretofore new device that overcome these shortcomings. In particular, a device for treating arterial occlusive disease is provided that includes a plurality of hollow tubes as well as first and second cutting baskets at a distal end of the device. A first tubular shaft member is provided for the device. The first tubular shaft member extends along a longitudinal axis from a proximal end to a distal end. A second hollow tubular shaft member coaxial to the first tubular shaft member is provided that extends along the longitudinal axis from the proximal end to the distal end. A third hollow tubular shaft member coaxial to the first and second hollow tubular members is provided that extends along the longitudinal axis. The third hollow tubular shaft member is connected to a first cutting basket proximate the distal end. A second cutting basket is connected to the second hollow tubular shaft member proximate the distal end. The second hollow tubular shaft member is connected to a rotary drive source proximate the proximal end to rotate the second cutting basket relative to the first cutting basket about the longitudinal axis. The second cutting basket and the first cutting basket are coupled to the first tubular shaft member so that translation of the first tubular shaft member along the longitudinal axis changes a diameter of at least the second cutting basket between a first diameter to a second diameter greater than the first diameter while the second cutting basket rotates about the longitudinal axis.

In yet another embodiment, a first tubular shaft member is provided that extends along a longitudinal axis from a proximal end to a distal end. A second hollow tubular shaft member coaxial to the first tubular shaft member is provided that extends along the longitudinal axis from the proximal end to the distal end. A third hollow tubular shaft member coaxial to the first and second hollow tubular members is provided that extends along the longitudinal axis. The third hollow tubular shaft member is connected to both a first cutting basket as well as the first hollow tubular member. A second cutting basket is connected to the second hollow tubular member. The second hollow tubular shaft member is connected to a rotary drive source to rotate the second cutting basket relative to the first cutting basket about the longitudinal axis. The second cutting basket and the first cutting basket are coupled to the first tubular shaft member so that translation of the first tubular shaft member along the longitudinal axis changes a diameter of at least the second cutting basket between a first diameter to a second diameter greater than the first diameter while the second cutting basket rotates about the longitudinal axis. It is noted that while the diameter of the first cutting basket and the diameter of the second basket can change independently (via respective shafts), the preference is to have both respective diameters of the first and second cutting baskets change in unison.

In yet a further embodiment, a first tubular shaft member is provided that extends along a longitudinal axis from a proximal end to a distal end. A second hollow tubular shaft member coaxial to the first tubular shaft member is provided that extends along the longitudinal axis from the proximal end to the distal end. A third hollow tubular shaft member coaxial to the first and second hollow tubular members is provided that extends along the longitudinal axis. The third hollow tubular shaft member is connected to both a first cutting basket as well as the first hollow tubular member. A second cutting basket is connected to the second hollow tubular member. The second hollow tubular shaft member is connected to a rotary drive source to rotate the second cutting basket relative to the first cutting basket about the longitudinal axis. The second cutting basket and the first cutting basket are coupled to the first tubular shaft member so that translation of the first tubular shaft member along the longitudinal axis changes a diameter of the second cutting basket continuously from a first diameter to a second diameter greater than the first diameter while the second cutting basket rotates about the longitudinal axis.

In yet still another embodiment, a system for treating arterial occlusive disease is provided. The system includes a control handle proximate an operator. The control handle includes a control lever, an infusion port and an aspiration port, a rotary power source and a vacuum source connected to the aspiration port. The control handle is coupled to a cutting catheter having a working end at a distal end of the device. The cutting catheter includes a first hollow tubular member. The first tubular shaft member extends along a longitudinal axis from a proximal end to a distal end of the system. A second hollow tubular shaft member coaxial to the first tubular shaft member is provided that extends along the longitudinal axis from the proximal end to the distal end. A third hollow tubular shaft member coaxial to the first and second hollow tubular members is provided that extends along the longitudinal axis. The third hollow tubular shaft member is connected to a first cutting basket proximate the distal end. A second cutting basket is connected to the second hollow tubular shaft member proximate the distal end. The second hollow tubular shaft member is connected to a rotary drive source proximate the proximal end and controlled by a control switch to rotate the second cutting basket relative to the first cutting basket about the longitudinal axis. The second cutting basket and the first cutting basket are coupled to the first tubular shaft member so that continuous translation of the first tubular shaft member via the control lever along the longitudinal axis changes a diameter of the second cutting basket infinitely from a first diameter to a second diameter greater than the first diameter while the second cutting basket rotates about the longitudinal axis.

Alternative embodiments of the invention can be achieved when utilized with other features noted hereafter with the embodiments referenced earlier. For example, the first cutting basket may include at least two rotary cutting blades each defining a curvilinear thin edge member that extends along the longitudinal axis to define an arcuate edge as viewed in a sectional view taken on a plane orthogonal to the longitudinal axis; the second cutting basket may include at least two rotary cutting blades each defining a curvilinear thin edge member that extends along the longitudinal axis to define an arcuate edge about the longitudinal axis; the first and second cutting baskets are may include from a shape memory material; the shape memory material may include Nitinol; the first cutting basket is heat-set to a compressed state and the second cutting basket is heat-set to an expanded and uncompressed state at or above a phase transition temperature; both the first and second cutting baskets are heat-set to an expanded state above a phase transition temperature; the first cutting basket is stationary; the first cutting basket is configured to rotate in a direction opposite a direction of the second cutting basket; saline solution is pumped through a flow passage (102a) the first tubular shaft member to the distal end proximate the first cutting basket; a vacuum source is coupled to an aspiration port defined by a gap formed between the second and third hollow tubular members.

These and other embodiments, features and advantages will become apparent to those skilled in the art when taken with reference to the following more detailed description of the exemplary embodiments of the invention in conjunction with the accompanying drawings that are first briefly described.

BRIEF DESCRIPTION OF DRAWINGS

The patent or application file contains at least one drawing executed in color. Copies of this patent or patent application publication with color drawings will be provided by the Office upon request and payment of the necessary fee.

The accompanying drawings, which are incorporated herein and constitute part of this specification, illustrate presently preferred embodiments of the invention, and, together with the general description given above and the detailed description given below, serve to explain features of the invention wherein like numerals represent like elements, in which:

FIG. 1 is an illustration of an exemplary system for the claimed invention;

FIG. 2 is a close-up partial sectional view of the catheter 100;

FIG. 3 is an end-view as indicated in the dashed lines 3-3 of FIG. 2;

FIGS. 9 and 10 are close-up photographs from a side view of a prototype of an embodiment in which FIG. 9 shows a first outer diameter operational configuration while FIG. 10 shows a final maximum outer diameter operational configuration.

MODES OF CARRYING OUT THE INVENTION

Figure 4:
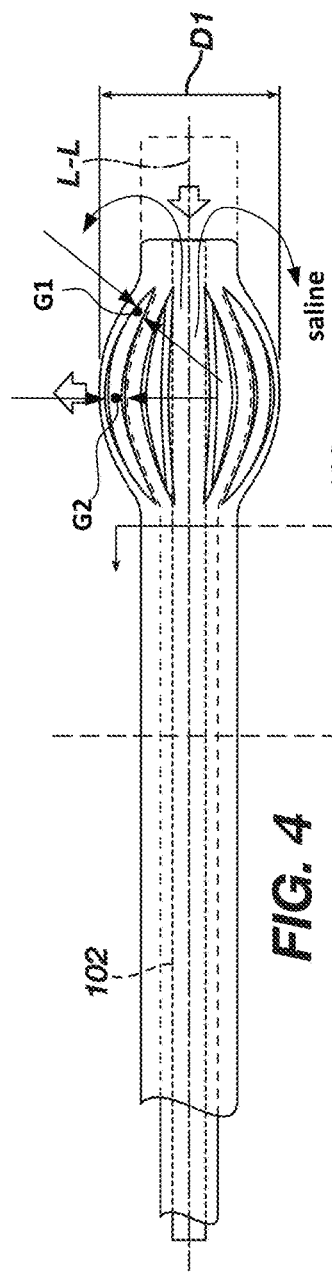
FIG. 4 is a side view of the catheter 100 in a starting position after the shaft 102 is translated proximally to increase the basket outer diameter from a minimum diameter D to a starting diameter of D1.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the root terms "distal" or "proximal" are referenced in relation to a user in which "distal" indicates that certain parts or components are further away to the user and "proximal" indicates that certain parts or components are closer to the user. It is noted that the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

The following description provides specific details for a thorough understanding of, and enabling description for, embodiments of the invention. However, one skilled in the art will understand that the invention may be practiced without these details. In other instances, well-known structures and functions have not been shown or described in detail to avoid unnecessarily obscuring the description of the embodiments of the invention.

Referring now to the figures wherein like numerals indicate the same element throughout the views, there is shown in FIG. 1 a system 10 for treating arterial occlusive disease with a control handle 200. Control handle 200 is provided with a trigger arm 202, control switch 203 (for motor 300), saline inlet port 204, and an aspiration outlet 206 connected to a vacuum source that may have a pressure regulator to control the aspiration rate of plaque debris previously dislodged by the cutting catheter device 100. A motor 300 (e.g., DC or pneumatic with sufficient speed and torque) can be built into the handle 200 and coupled mechanically to the cutting catheter 100 so as to impart rotary motion to the cutting members of the cutting catheter 100. The motor 300 can be controlled by one of the trigger 202 or the switch 203 for variable speed and torque using suitable control techniques including for example pulse width modulation or PID control.

With reference to FIG. 2, a close up partial cross-sectional view of the cutting catheter 100 is shown that can be used to treat arterial occlusive disease (e.g., atherectomy or thrombectomy). Specifically, cutting catheter 100 extends along a longitudinal axis L-L in a blood vessel with typical plaque buildup on the vessel wall. As shown here, the catheter 100 is intended to be used without the need for a delivery catheter. Nevertheless, where suitable, a delivery catheter 101 can be used to guide the cutting catheter 100 to the lesion site.

A description of the components in cutting catheter 100 will now be described. Starting from the longitudinal axis L-L and moving radially outward, catheter 100 is provided with a first tubular shaft member 102 that extends along the longitudinal axis L-L from a proximal end, i.e., the portion closest to the operator, to a distal end, i.e., the portion further away from the operator. Coaxial to the first tubular shaft member 102 is a second hollow tubular shaft member 104. The second hollow tubular shaft member 104 is coaxial along the longitudinal axis L-L from the proximal end to the distal end. Moving further radially outward from axis L-L, a third hollow tubular shaft member 106 is also disposed coaxial to the first and second hollow tubular members 102 and 104, respectively, along the longitudinal axis L-L. The third hollow tubular shaft member 106 is directly connected to a first cutting basket 108 such that the tubular member 106 and the first cutting basket 108 rotate as one unit. While the first tubular shaft 102 is shown as hollow to allow the use of a guidewire GW, the first tubular shaft 102 can be configured so that it is a solid shaft where a guidewire is not needed or good column strength is desired (via a solid shaft 102) for the device 100 during the cutting procedure.

Details of the first cutting basket 108 can be seen in the end on view in FIG. 3. In this end view, it can be seen that the cutting basket 108 can be formed by at least one flexible and thin surface 108a. In particular, it is intended that there be at least two rotary cutting blades 108a each defining a curvilinear thin-edge member 108b that extends along the longitudinal axis to define a generally arcuate edge 108c, as viewed by an observe 120 on a plane orthogonal to the longitudinal axis L-L, shown here in FIG. 3. Because of the very thin surface of the curvilinear cutting member 108a, for example 400 microns or less, indicated here at 108b, with the cutting edge 108c having a thickness of about 200 microns or less depending on the tissue thickness and characteristics, the cutting basket 108 can cut through virtually if not all types of plaque present in a typical lesion. Although the thin edge member is shown as arcuate, the member can be configured to have its cutting edge angled (radially inward or outward) to achieve a desired cutting action.

Referring back to FIG. 2, a second and smaller cutting basket 110 is connected to the second hollow tubular shaft member 104. Similar to the first cutting basket 108, the second cutting basket 110 has at least two rotary cutting blades 110a. Each blade 110a defines a curvilinear thin edge member 110b that extends along the longitudinal axis to define an arcuate edge 110c as viewed in a sectional view taken on a plane 120 orthogonal to the longitudinal axis L-L, shown here in FIG. 3. Both of the first and second cutting baskets can be formed of a shape memory material, such as, for example, Nitinol. Alternatively, the cutting baskets 108 and 110 can be formed from a non-metallic high strength material such as graphene as well as combination of metal material combined with diamonds or carbide cutting edge. The shape set of the first cutting basket 108 can be devised so that basket 108 has a different radius of curvature as compared to the second cutting basket 110. This arrangement, shown here in FIG. 4, allows for the leading edge of the two baskets to have a smaller gap G1 between the two cutting surfaces while providing for a larger gap G2 between the two cutting baskets.

Where the cutting baskets are formed from Nitinol, it is intended that the first cutting basket 108 is heat-set to a compressed state (i.e., unexpanded state of substantially the same diameter as the catheter 100) and the second cutting basket 110 is heat-set to an expanded (i.e., uncompressed state of a diameter greater than the diameter of catheter 100) state at or above a phase transition temperature, such as for example, 37 degrees Celsius. By configuring the cutting baskets this way, the second cutting basket 110 will be urged into close contact with the first cutting basket 108. Alternatively, both the first and second cutting baskets are heat-set to an expanded state above phase transition temperature so that in the presence of ambient temperature at or above a phase transition temperature, the baskets are urged into an expanded diameter greater than the diameter of the catheter 100.

In an alternate embodiment, the inner cutting basket 110 is set so that it tends to remain in a somewhat straight configuration so as to maintain a smaller diameter whereas the outer cutting basket 108 is set so that it tends to expand into a greater diameter. In yet a further embodiment, the inner cutting basket 110 is set so that it tends to expand into a greater diameter whereas the inner cutting basket 110 is set so that it tends to remain in a somewhat straight configuration so as to maintain a smaller diameter.

The second hollow tubular shaft member 104 is connected to a rotary drive source 300 (e.g., electric or pneumatic) to rotate the second cutting basket 110 relative to the first cutting basket 108 about the longitudinal axis L-L during the atherectomy procedure. In one embodiment, the second cutting basket 110 and the first cutting basket 108 are coupled (e.g., roller bearing 119a or plain bearing 119b) to the first tubular shaft member 102 to allow for relative rotation of the two baskets. This coupling is made so that translation of the first tubular shaft member 102 along the longitudinal axis changes a diameter of at least the second cutting basket between a first diameter D1 to a second diameter D2 greater than the first diameter D1 of at least the second cutting basket 110 while the second cutting basket 110 rotates about the longitudinal axis L-L.

Figure 5:
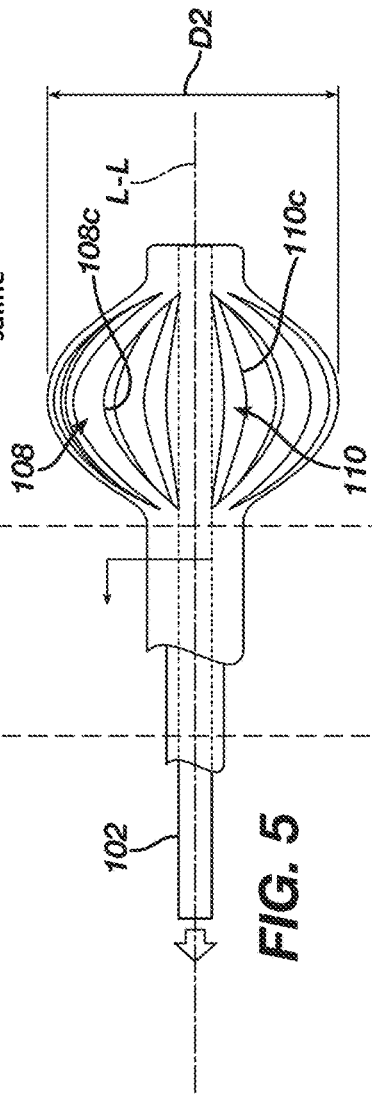
FIG. 5 is a side view of the catheter 100 with the first hollow shaft 102 translated towards the proximal end along longitudinal axis L-L to infinitely increase the outer diameter of the cutting basket from D1 to D2.
Figure 6:
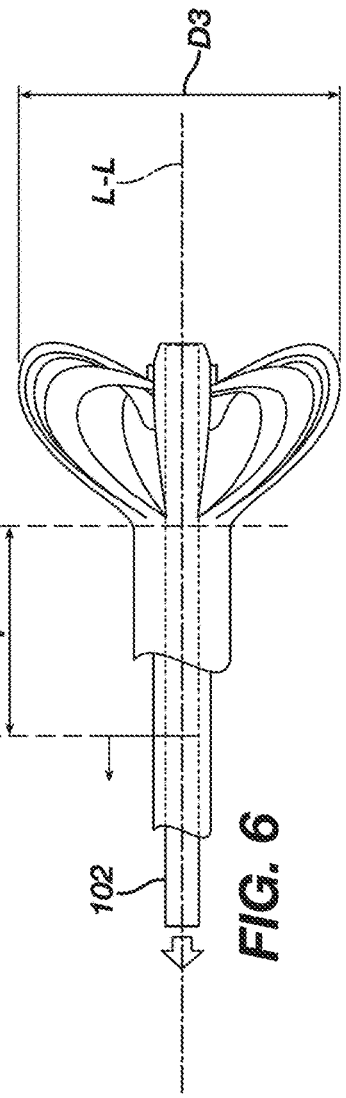
FIG. 6 is a side view of the catheter with the first hollow shaft 102 further translated proximally along axis L-L to increase the outer diameter from D2 to D3.

The infinitely adjustable cutting diameter is illustrated in FIGS. 4-6. In FIG. 4, the cutting baskets 108 and 110 have been translated via movement of the hollow shaft 102 into an initial working diameter D1. In this position, the cutting baskets are able to engage with the plaque buildup. While the initial working diameter D1 is shown here, it is noted that the starting diameter D of the cutting basket is intended to be smaller and not significantly greater than the outermost diameter of the catheter 100. In most instances, the starting outer diameter of the outer cutting basket will be substantially the same as the inner diameter of the delivery catheter. Once the delivery catheter is retracted to expose the cutting baskets, the operator will start successively increase the outer diameter of the cutting baskets so that over a number of passes back and forth, the device will be able to clear out a large occlusion in a large artery or vessel.

In FIG. 5, the tubular shaft 102 can be translated via pivoting movement of the trigger 202 on the handle 200 towards the proximal end to further increase the working diameter of the cutting basket (towards a larger second working diameter D3). The adjustment of the basket diameters will cause the gap G2 between the two baskets in FIG. 4 to decrease even more such that the two baskets are even closer in FIG. 5. Further translation of tubular shaft 102 towards the proximal end will increase the working diameter to a maximum working diameter D3 that can be configured to work with the largest biological vessel without damaging the vessel wall. In the embodiments described herein, D is about 1.2 mm, D1 is about 1.6 mm, D2 is about 2.0 mm and D3 is about 3.5 mm.

In the embodiments described above, the first cutting basket can be configured to be stationary such that when the first cutting basket 108 impinges onto the vessel wall or plaque, little or no damage can occur by this contact of the first cutting 108 onto the vessel wall. When plaque removal is desired, the first cutting basket 108 can remain stationary while the second cutting basket 110 begins rotating about the longitudinal axis L-L with control of motor 300 via switch 203.

In situations where additional cutting force may be desired, the first cutting basket 108 can be connected to the motor 300 via a suitable drive transfer mechanism to allow for rotation in the direction opposite (i.e., a contra or counter-rotation) to that of the second cutting basket 110. The first and second cutting baskets 108, 110 can be connected via a flexible drive in the form of a hollow and flexible "torque tube" (e.g., thin-wall polymeric tubing with an intermediate layer of braided or woven wire, and an outer polymeric layer).

In one embodiment, the torque tube may include a polyimide tube with a wall thickness of about 0.1 mm and a layer of braided 0.04 mm stainless steel wire embedded therein. The outer diameter of such torque tube(s) is about 0.5 mm to about 1 mm. The internal diameter of the first hollow tube 102 can be slightly greater than the typical 0.018 inch guidewire diameter. The catheter 100 can be formed from, for example, PEBAX extrusion with an outside diameter that may vary from about 1.5 mm to about 4 mm (or more) depending on the intended use at a particular location of the body vessel. The thickness of the catheter 100 is about 0.1 mm or more in order to resist collapse due to vacuum forces generated for aspiration.

Referring back to FIG. 1, saline (or any biocompatible solution) can be infused or pumped into the distal end of catheter 100 (proximate first cutting basket 108) via infusion port 204 which may have a valve to allow the use of a Luer lock fitting. Suitable seals are provided in the handle to allow flow of fluid from the port 204 to the distal end of catheter 100. Disposed in the handle 200 is a Y-type port to allow the connection of a vacuum source to the generally annular space 114 defined by the gap 112 between one of the first shaft 102, second shaft 104, and third shaft 106. This allows for plaque debris 118 removed from the lesion to be aspirated via from outside of the gaps 130 formed between the two cutting baskets (108 and 110) into the annular space 114.

Figure 7:
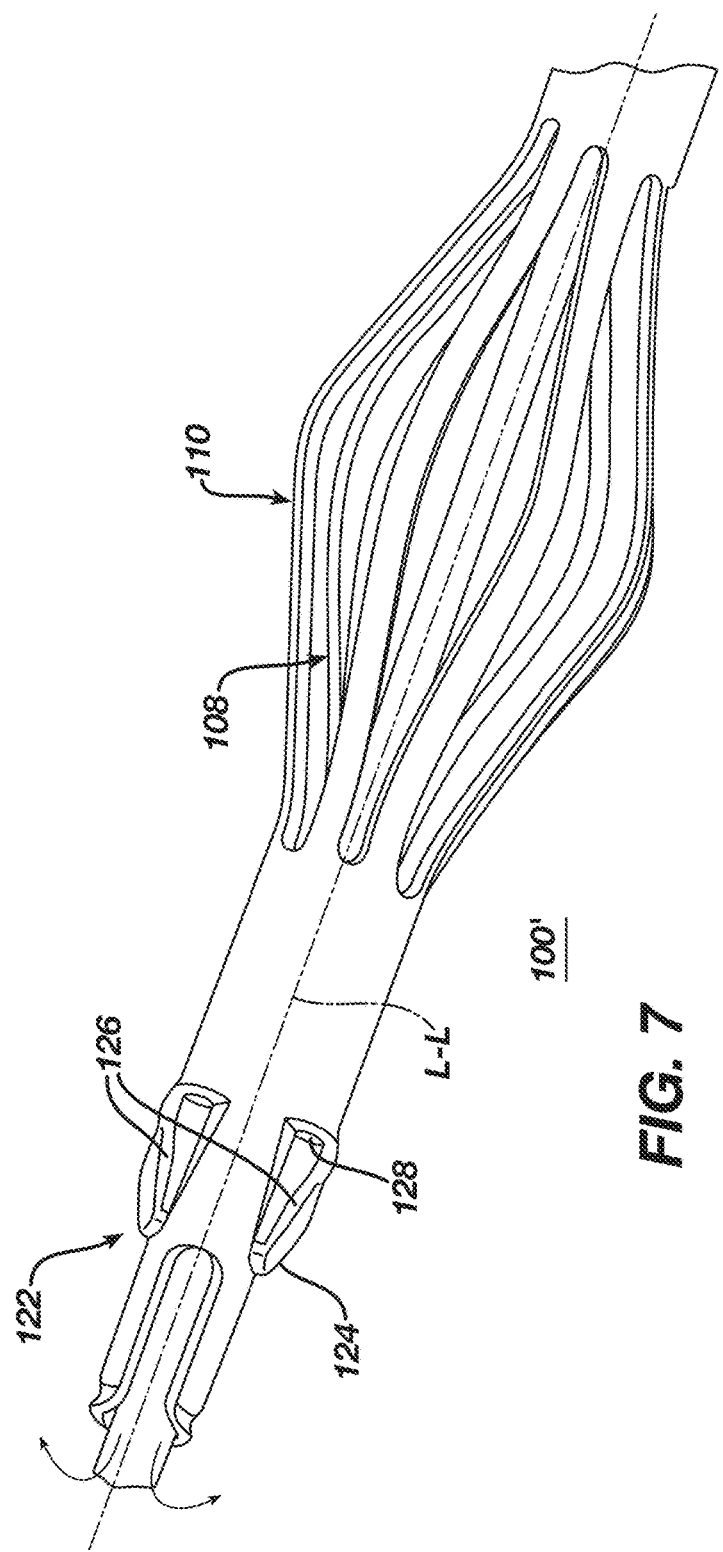
FIG. 7 is another embodiment of the cutting catheter with a distal frontal cutting basket to assist in the initial penetration or dislodgement of heavily calcified plaques.

FIG. 7 illustrates another embodiment 100' (of catheter 100) in which a third cutting basket is disposed at the distal end of catheter 100' to act as the frontal cutting basket 122. The frontal cutting basket 122 is smaller than the main cutting baskets 108 and 110 to allow ease of entry into the plaques. In this embodiment, the basket 122 is connected to first tube 102 to allow for changes in its working diameter as well as rotation of the front cutting basket 122 (and outer basket 110). Because the frontal cutting head 122 has a much smaller working diameter as well as smaller cutting edge (formed by a conic shaped curvilinear surface 124 with sharp edges 126), much more pressure can be applied with the same amount of force by the pre-cutting basket 122 onto the plaque surfaces. As before, saline can be infused or pumped out of the tip of catheter 100' and aspirated back into the catheter 100' and the collection container via aspiration ports 128.

Figure 8:
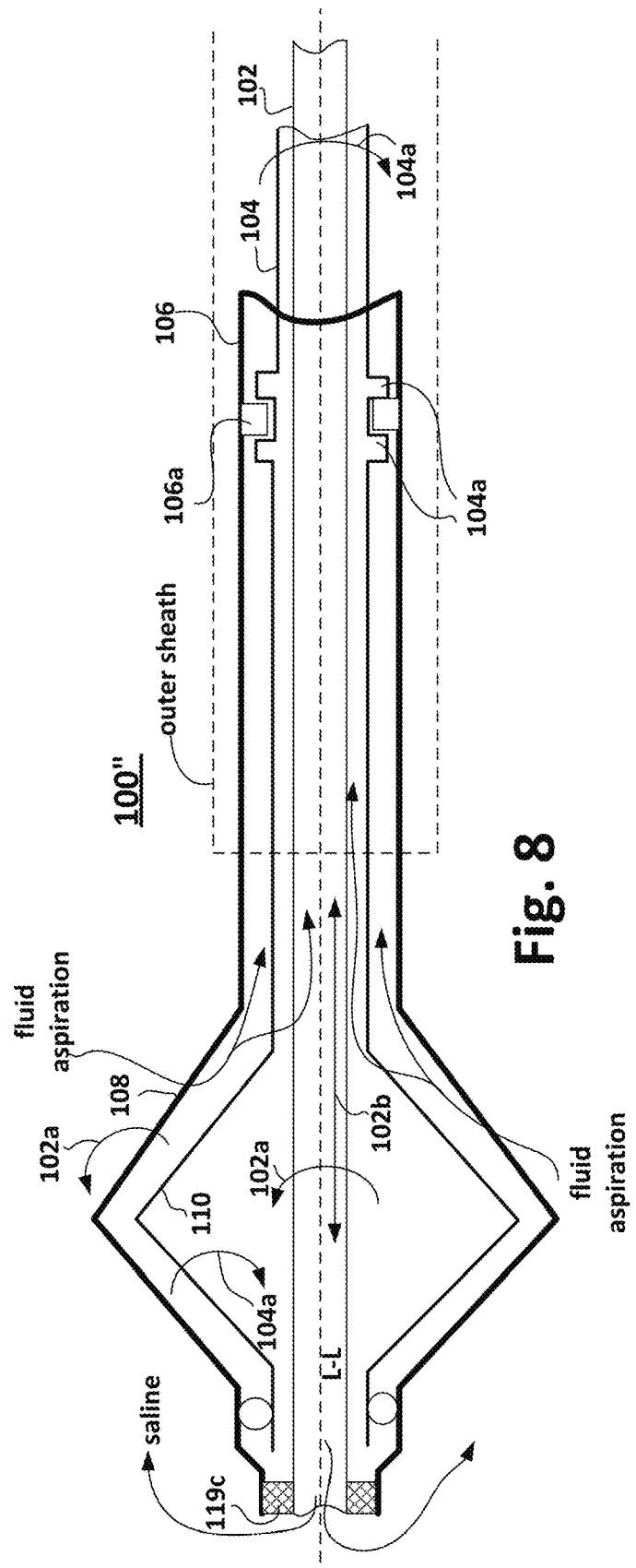
FIG. 8 illustrates in schematic form the components of another embodiment of the device.

FIG. 8 illustrates in schematic form the components of yet another embodiment 100". In this embodiment, first hollow tube 102 is also the guidewire lumen and for saline infusion. The outer basket 108 as well as third hollow shaft 106 is fixed for rotation with first hollow shaft 102 via a retention member 119c (e.g., a key and slot or a bonded arrangement) while the inner basket 110 is fixed for rotation with second hollow shaft 104. The inner basket 110 is allowed to rotate at the distal end. Axial fixation mechanism (104a and 106a) in FIG. 8 allows the two baskets to rotate relative to one another while maintaining fixation between the two baskets. The axial fixation mechanism is in the form of inner boss 106a being captured between a slot formed by two parallel outer bosses 104a. As with the prior embodiments, first shaft 102 rotates in direction 102a and can be translated along direction 102b. Rotation or translation of shaft 102 causes the outer basket 108 to rotate but due to the third shaft 106 being axially captured at 106a, outer basket 108 would change its outer diameter to allow for shaft 102 to translate. In the event the shaft 102 is translated distally (towards the operator) a gap may be built in at the distal end proximate fixation member 119c to allow for a slack before fixation member 119c engages the inner basket 110 which will eventually cause the inner basket to increase in its outer diameter. In one embodiment, there may be a sheath over all of the components shown here but which is retracted to expose the inner and outer cutting baskets 110 and 108. It is noted here that the inner basket 110 can rotate in a direction 104a opposite the rotation 102a of the outer basket 108. Alternatively, the outer basket 108 can be maintained stationary with respect to the inner basket 110.

Figure 9:
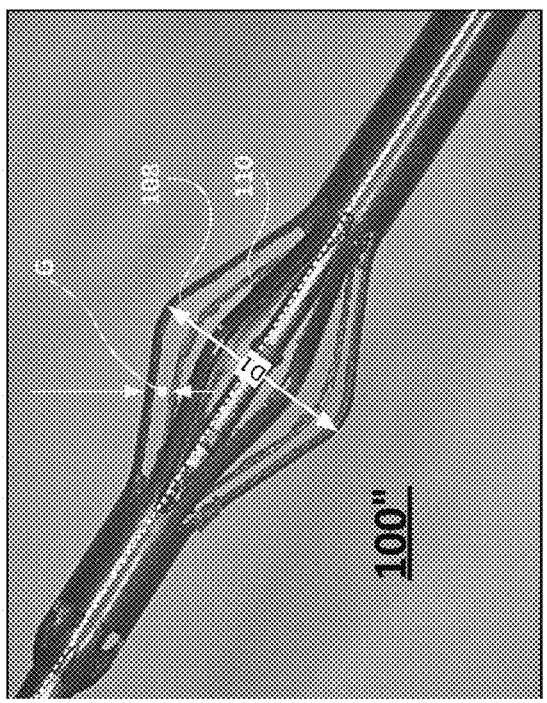
Figure 10:
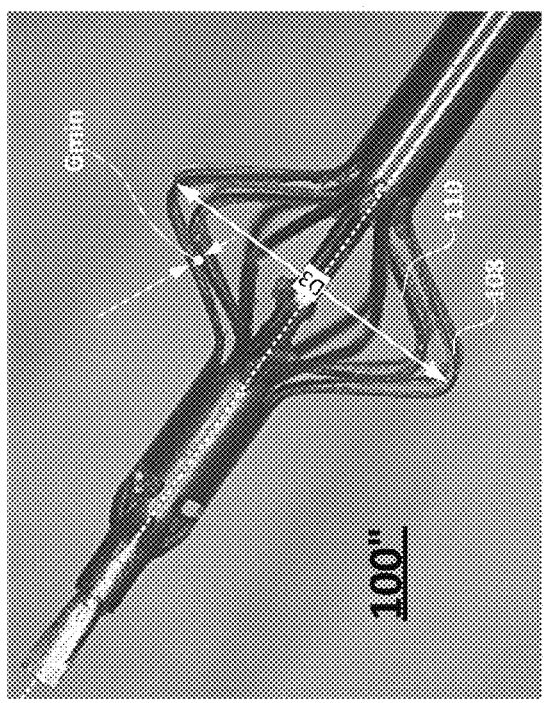

FIGS. 9 and 10 are close up color photograph of a prototype for device 100" shown earlier (in the schematic form of FIG. 8). In FIG. 9, it is noted that the first operational diameter D1 allows for a gap G between the inner basket 110 and outer basket 108. As an inner shaft 102 is pulled back, this forces the outer basket 108 to expand and also the inner basket 110 to also expand. Due to the different curvatures set for the inner and outer baskts, the gap G in the initial diameter D1 is reduced (when both baskets are expanded to D3) until a minimum gap Gmin is achieved in FIG. 10 at a location other than the maximum outer diameter of each of the inner and outer cutting baskets 110 and 108.

In use, a small incision is made on a patient, typically in the femoral artery. An access or introducer sheath is utilized to gain access to the artery via the incision. A guidewire and a guide catheter (e.g., 101) may be used to allow access of the cutting catheter 100 (or 100') to the occlusion or lesion site, as is well known in the art and therefore needs not belabored here. It is noted that saline, drugs or contrast solution can be infused at any time during this procedure as required by the operator. Additionally, during the procedure, vacuum can be coupled to extract the debris, saline and body fluids into a container proximate the handle 200.

Once the cutting catheter 100 (or 100') reaches the intended site, plaque removal can begin. With the cutting baskets 108 and 110 remaining in their initial diameter D, the second basket 110 can be rotated relative to the first basket 108 or both baskets contra-rotating to initiate the plaque excision. When suitable, the first hollow tube 102 may be retracted proximally via trigger 202 to increase the outside diameter of the first and second cutting baskets (108, 110). The changes in the outside diameter of the cutting basket(s) can be infinitely increased from D to D1 to D2 while ensuring that the cutting baskets are generally coaxial to the centerline of the body vessel, i.e., a "centering effect" in the vessel while also cutting through the plaques. This "centering" effect of the cutting baskets is believed to reduce or even eliminate the tendency of the catheter 100 to whip uncontrollably around in the body vessel which may cause trauma or perforation to the vessel walls.

Moreover, the continuous adjustment of the outside diameter of basket 108 or basket 110 is believed to allow for very fine removal of the plaque with little or no injury to the underlying blood vessel just below the plaque surface. It is believed that the exemplary device (via its various embodiments) allows an operator to finely adjust and infinitely vary the cutting baskets' working diameter to adapt to the plaque while in-situ. Consequently, an experienced operator is able to quickly remove large amount of plaques without the fear of the catheter 100 whipping around uncontrollably inside the vessel. Due to the ability of the operator to infinitely adjust the outer diameter of the cutting baskets, embodiments of the present invention are not limited to atherectomy but can also be used as a thrombectomy device to remove blood clots.

While the invention has been described in terms of particular variations and illustrative figures, those of ordinary skill in the art will recognize that the invention is not limited to the variations or figures described. In addition, where methods and steps described above indicate certain events occurring in certain order, it is intended that certain steps do not have to be performed in the order described but in any order as long as the steps allow the embodiments to function for their intended purposes. Therefore, to the extent there are variations of the invention, which are within the spirit of the disclosure or equivalent to the inventions found in the claims, it is the intent that this patent will cover those variations as well.

What is claimed is:

1. A device for treatment of arterial occlusive disease comprising:
   a first tubular shaft member that extends along a longitudinal axis from a proximal end to a distal end;
   a second hollow tubular shaft member coaxial to the first tubular shaft member along the longitudinal axis and enclosed from the proximal end to the distal end, and further configured to have a constant diameter during use of the device;
   a third hollow tubular shaft member coaxial to the first tubular shaft member and the second hollow tubular member along the longitudinal axis, enclosed from the proximal end to the distal end and configured to have a constant diameter during use of the device, the third hollow tubular shaft member being connected to a first cutting basket; and
   a second cutting basket connected to the second hollow tubular shaft member, the second hollow tubular shaft member being connected to a rotary drive source to rotate the second cutting basket relative to the first cutting basket about the longitudinal axis, the second cutting basket and the first cutting basket being coupled to the first tubular shaft member so that translation of the first tubular shaft member along the longitudinal axis changes a diameter of the second cutting basket continuously from a first diameter to a second diameter greater than the first diameter while the second cutting basket rotates about the longitudinal axis.

2. The device of claim 1, in which the first cutting basket comprises at least two rotary cutting blades each defining a curvilinear thin edge member that extends along the longitudinal axis to define an arcuate edge as viewed in a sectional view taken on a plane orthogonal to the longitudinal axis.

3. The device of claim 1, in which the second cutting basket comprises at least two rotary cutting blades each defining a curvilinear thin edge member that extends along the longitudinal axis to define an arcuate edge about the longitudinal axis.

4. The device of claim 1, in which the first and second cutting baskets are comprise from a shape memory material.

5. The device of claim 4, in which the shape memory material comprises Nitinol.

6. The device of claim 5, in which the first cutting basket is heat-set to a compressed state and the second cutting basket is heat-set to an expanded and uncompressed state at or above a phase transition temperature.

7. The device of claim 5, in which both the first and second cutting baskets are heat-set to an expanded state above a phase transition temperature.

8. The device of claim 1, in which the first cutting basket is stationary.

9. The device of claim 1, in which the first cutting basket is configured to rotate in a direction opposite a direction of the second cutting basket.

10. The device of claim 1, in which saline solution is pumped through a flow passage of the first tubular shaft member to the distal end proximate the first cutting basket.

11. The device of claim 10, in which a vacuum source is coupled to an aspiration port defined by a gap formed between one of the first, second and third shaft members.

12. A device for treatment of arterial occlusive disease comprising:
   a first tubular shaft member that extends along a longitudinal axis from a proximal end to a distal end;
   a second hollow tubular shaft member coaxial to the first tubular shaft member along the longitudinal axis and enclosed from the proximal end to the distal end, further configured to have a constant diameter during use of the device;
   a third hollow tubular shaft member coaxial to the first tubular shaft member and second hollow tubular shaft member along the longitudinal axis, enclosed from the proximal end to the distal end and configured to have a constant diameter during use of the device, the third hollow tubular shaft member being connected to both a first cutting basket as well as the first tubular shaft member; and a second cutting basket connected to the second hollow tubular shaft member, the second hollow tubular shaft member being connected to a rotary drive source to rotate the second cutting basket relative to the first cutting basket about the longitudinal axis the second cutting basket and the first cutting basket being coupled to the first tubular shaft member so that translation of the first tubular shaft member along the longitudinal axis changes a diameter of the second cutting basket infinitely from a first diameter to a second diameter greater than the first diameter while the second cutting basket rotates about the longitudinal axis.

13. The device of claim 12, in which the first cutting basket comprises at least two rotary cutting blades each defining a curvilinear thin edge member that extends along the longitudinal axis to define an arcuate edge as viewed in a sectional view taken on a plane orthogonal to the longitudinal axis.

14. The device of claim 12, in which the second cutting basket comprises at least two rotary cutting blades each defining a curvilinear thin edge member that extends along the longitudinal axis to define an arcuate edge about the longitudinal axis.

15. The device of claim 12, in which the first and second cutting baskets are comprise from a shape memory material.

16. The device of claim 15, in which the shape memory material comprises Nitinol.

17. The device of claim 16, in which the first cutting basket is heat-set to a compressed state and the second cutting basket is heat-set to an expanded and uncompressed state at or above a phase transition temperature.

18. The device of claim 16, in which both the first and second cutting baskets are heat-set to an expanded state above a phase transition temperature.

19. The device of claim 12, in which the first cutting basket is stationary.

20. The device of claim 12, in which the first cutting basket is configured to rotate in a direction opposite a direction of the second cutting basket.

* * * * *